United States Patent [19]
Edwards et al.

[11] Patent Number: 5,507,743
[45] Date of Patent: Apr. 16, 1996

[54] COILED RF ELECTRODE TREATMENT APPARATUS

[75] Inventors: Stuart D. Edwards, Los Altos; Hugh R. Sharkey, Redwood Shores, both of Calif.

[73] Assignee: ZoMed International, Mountain View, Calif.

[21] Appl. No.: 291,424

[22] Filed: Aug. 16, 1994

Related U.S. Application Data

[63] Continuation-in-part of Ser. No. 148,439, Nov. 8, 1993, Pat. No. 5,458,597.

[51] Int. Cl.⁶ ................................................. A61B 17/39
[52] U.S. Cl. .................. 606/41; 606/48; 607/101; 607/154; 607/156; 128/642
[58] Field of Search ................ 606/32–34, 37–42, 606/45–50; 128/642; 607/100–102, 115, 116, 154–156

[56] References Cited

U.S. PATENT DOCUMENTS

| | | |
|---|---|---|
| 4,154,246 | 5/1979 | LeVeen . |
| 4,409,993 | 10/1983 | Furihata . |
| 4,565,200 | 1/1986 | Cosman ................................ 128/642 |
| 4,583,556 | 4/1986 | Hines et al. . |
| 4,676,258 | 6/1987 | Inokuchi et al. . |
| 4,763,671 | 8/1988 | Goffinet . |
| 4,825,880 | 5/1989 | Stauffer et al. . |
| 4,846,196 | 7/1989 | Wiksell et al. . |
| 4,907,589 | 5/1990 | Cosman ................................ 606/34 |
| 4,920,978 | 5/1990 | Colvin . |
| 5,246,438 | 9/1993 | Langberg ............................... 606/33 |
| 5,249,585 | 10/1993 | Turner et al. ......................... 607/99 |
| 5,259,395 | 11/1993 | Li ........................................ 128/642 |
| 5,300,099 | 4/1994 | Rudie .................................. 607/101 |
| 5,383,876 | 1/1995 | Nardella .............................. 606/50 |
| 5,403,311 | 4/1995 | Abele et al. .......................... 606/49 |
| 5,405,346 | 4/1995 | Grundy et al. ...................... 606/41 |

*Primary Examiner*—Stephen C. Pellegrino
*Assistant Examiner*—Michael Peffley
*Attorney, Agent, or Firm*—Haynes & Davis

[57] ABSTRACT

An RF treatment apparatus provides multi-modality treatment for tumors and other desired tissue masses, and includes an RF indifferent electrode and an RF active electrode. The RF indifferent electrode has a compacted, non-deployed state, and an expanded deployed state. In the deployed state, the RF indifferent electrode forms a helical structure with four or less coils that surround an exterior of the tumor. The indifferent electrode becomes a microwave antenna when it is coupled to a microwave source. RF ablation energy is delivered to the tumor by the RF active electrode after it has been introduced into the tumor. Both electrodes are coupled to an RF energy source. The indifferent electrode is coupled to a microwave source. Either or both of the electrodes is hollow and include fluid distribution ports for the purpose of providing a chemotherapeutic agent to the tumor site. Ablation energy is supplied to the tumor by the active electrode. The RF indifferent electrode then is switched and becomes a microwave antenna, providing hyperthermia to the tumor and surrounding area. Thereafter, a chemotherapeutic agent is supplied to the tumor site.

41 Claims, 9 Drawing Sheets

COILED RF ELECTRODE TREATMENT APPARATUS

This application is a continuation-in-part of U.S. patent application Ser. No. 08/148,439, filed on Nov. 8, 1993 now U.S. Pat. No. 5,458,597, entitled "DEVICE FOR TREATING CANCER AND NON-MALIGNANT TUMORS AND METHODS", by Edwards et al. which is incorporated herein by reference.

BACKGROUND OF THE INVENTION

1. Field of the Invention

This invention relates generally to an RF electrode apparatus used in the treatment of tumors and, more particularly, to a coiled RF electrode apparatus that surrounds a volume of a tissue target for desiccation of the tissue and provides both ablation and hyperthermia treatment of the tumor.

2. Description of the Related Art

Current open procedures for treatment of tumors are extremely disruptive and cause a great deal of damage to healthy tissue. Accordingly, there has recently been a fair amount of emphasis on minimally invasive procedures for tissue destruction and removal.

It is known that elevating the temperature of tumors is helpful in the treatment and management of cancerous tissues. The mechanisms of selective cancer cell eradication by hyperthermia is not completely understood. However, four cellular effects of hyperthermia on cancerous tissue have been proposed, (i) changes in cell or nuclear membrane permeability or fluidity, (ii) cytoplasmic lysomal disintegration, causing release of digestive enzymes, (iii) protein thermal damage affecting cell respiration and the synthesis of DNA and RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the body. Certain techniques have been developed with microwave radiation and ultrasound to focus energy at various desired depths. RF applications may be used at depth during surgery. However, the extent of localization is generally poor with the result that healthy tissue may be harmed. Induction heating gives rise to poor localization of the incident energy as well. Although induction heating may be achieved by placing an antenna on the surface of the body, superficial eddy currents are generated in the immediate vicinity of the antenna when it is driven using RF current, and unwanted surface heating occurs with little coupled to the underlying tissue. Thus, non-invasive procedures for providing heat to internal tumors have had difficulties in achieving substantial specific and selective treatment.

Hyperthermia, which can be from an RF or microwave source, applies heat to tissue but does not exceed 45 degrees C. so that normal cells survive. In thermotherapy, heat energy of greater than 45 degrees C. is applied, resulting in histological damage and the denaturalization of proteins. Hyperthermia has been applied more recently for therapy of malignant tumors. In hyperthermia, it is desirable to induce a state of hyperthermia that is localized by interstitial current heating to a specific area while concurrently insuring minimum thermal damage to healthy surrounding tissue. Often, the tumor is located subcutaneously and addressing the tumor requires either surgery, endoscopic procedures or external radiation. It is difficult to externally induce hyperthermia in deep body tissue because current density is diluted due to its absorption by healthy tissue. Additionally, a portion of the RF energy is reflected at the muscle/fat and bone interfaces which adds to the problem of depositing a known quantity of energy directly on a small tumor.

Attempts to use interstitial local hyperthermia have not proven to be very successful. Results have often produced nonuniform temperatures throughout the tumor. It is believed that tumor mass reduction by hyperthermia is related to thermal dose. Thermal dose is the minimum effective temperature applied throughout the tumor mass for a defined period of time. Because blood flow is the major mechanism of heat loss for tumors being heated, and blood flow varies throughout the tumor, more even heating of tumor tissue is needed to ensure effective treatment.

The same is true for ablation of the tumor itself through the use of RF energy. Different methods have been utilized for the RF ablation of masses such as tumors. Instead of heating the tumor it is ablated through the application of energy. This process has been difficult to achieve due to a variety of factors including, (i) positioning of the RF ablation electrodes to effectively ablate all of the mass, (ii) introduction of the RF ablation electrodes to the tumor site and (iii) controlled delivery and monitoring of RF energy to achieve successful ablation without damage to non-tumor tissue.

There have been a number of different treatment methods and devices for treating tumors minimally invasively. One such example is an endoscope that produces RF hyperthermia in tumors, as disclosed in U.S. Pat. No. 4,920,978. A microwave endoscope device is disclosed in U.S. Pat. No. 4,409,993.

An apparatus for hyperthermic treatment of tumors is disclosed in U.S. Pat. No. 4,846,196. Two electrodes are connected to an RF energy source. One of the electrodes is shaped with an external surface the same size as the tumor area. It is used as the treatment electrode. The other electrode is an indifferent electrode and is in external contact with the skin of the body.

In U.S. Pat. No. 4,763,671 (the "'671 patent"), a minimally invasive procedure utilizes two catheters that are inserted interstitially into the tumor. The catheter includes a hard plastic support member. Around the support member is a conductor in the form of an open mesh. A layer of insulation is secured to the conductor with adhesive beads. It covers all of the conductor except a preselected length which is not adjustable. Different size tumors can not be treated with the same electrode. The device of the '671 patent fails to provide for the introduction of a fluidic medium, such as a chemotherapeutic agent, to the tumor for improved treatment.

In U.S. Pat. No. 4,565,200 (the "'200 patent"), an electrode system is described in which a single entrance tract cannula is used to introduce an electrode into a selected body site. The device of the '200 patent fails to provide for an electrode which surrounds the tumor for ablation or hyperthermia treatment.

However, none of these devices provide for the effective treatment of a tumor with RF energy that is used to ablate the tumor, introduce energy for hyperthermia, and finally introduce a chemotherapeutic agent.

It would be desirable to provide an RF treatment device that would be capable of ablation and hyperthermia as well as introduction of chemotherapeutic agent. Additionally, it would be an advancement to provide a device that would include at least one electrode which is advanced out of the distal tip of an introducing catheter and, as it is advanced, it becomes a wound electrode which continues to travel around the periphery of the outside of the tumor until substantially most of the tumor is surrounded by the electrode.

SUMMARY OF THE INVENTION

It is an object of the invention to provide an RF treatment apparatus that ablates tumors.

It is another object of the invention is to provide an RF treatment apparatus that ablates and provides hyperthermia to the tumor and surrounding tissue.

A further object of the invention is to provide an RF treatment apparatus that ablates, provides hyperthermia and introduces a chemotherapeutic agent to a tumor and it's surrounding area.

Still, a further object of the invention is to provide an RF treatment apparatus that has an indifferent electrode that forms a helical coil around an outside surface of the tumor.

Yet another object of the invention is to provide an RF treatment apparatus that includes an active electrode that is inserted into an interior of a tumor, and an indifferent electrode that, in a deployed state, forms a coil around an outside surface of the tumor.

Another object of the invention is to provide an RF treatment apparatus that has an indifferent electrode which forms a coil of variable pitch in the deployed state.

These and other objects of the invention are attained in an RF treatment apparatus adapted for treatment of a tumor. The apparatus includes an RF indifferent electrode having a compacted, non-deployed state, and an expanded deployed state. The RF indifferent electrode forms a helical structure with three or less coils in the deployed state that conform to an exterior surface of a tumor. The indifferent electrode becomes a microwave antenna when it is coupled to a microwave source and provides hyperthermia treatment to the tumor. An active electrode is introduced into the tumor to provide RF ablation of the tumor. An RF energy source is coupled to the electrodes. A microwave energy source is coupled to the indifferent electrode.

In one embodiment of the invention, the apparatus also includes an introducing trocar/catheter. The indifferent electrode has a variable pitch and forms a helix when it is in a deployed state. The active electrode provides ablation of the tumor. The indifferent electrode is hollow and includes a plurality of fluid distribution ports, suitable for introducing a chemotherapeutic agent to the tumor and the surrounding area around the tumor.

Because the pitch of the first electrode is variable, the physician is able to dial in the desired length and width of the indifferent electrode. One or more thermal sensors can be included and utilized to ascertain the temperature of the treatment area. This provides close monitoring and effective delivery, including dosage, of energy to treat the tumor.

In another embodiment of the invention, the indifferent electrode is made of a memory metal, such as nitinol, and as it is introduced out of the distal end of the introducing catheter it becomes shaped in a conical geometry to wrap around the exterior of the tumor. In the non-deployed position the indifferent electrode is much more compacted than in a deployed position and it fits easily in the introducing catheter.

A needle biopsy aspiration device can also be included in the RF treatment apparatus. It can be housed in the delivery catheter and extended to reach beyond the distal end of the delivery catheter in a deployed position to remove tissue from the tumor or the surrounding area. The biopsy device can be utilized to biopsy tissue prior to or after the treatment procedure is completed. It can be positioned along the edge of one of the electrodes.

The indifferent electrode becomes a microwave antenna to provide heat, hyperthermia, to the tumor and the surrounding tissue. One or more transponders may be included on either electrode for ultrasound imaging purposes.

The RF treatment apparatus of the invention ablates the tumor by the application of RF energy with the active electrode. The indifferent electrode serves as a hyperthermia source both to the tumor and to the surrounding tissue when it is used as a microwave antenna. Finally, the indifferent electrode is hollow, includes a plurality of fluid distribution ports and is adapted to receive one or more chemotherapeutic agents that are delivered to the tumor and the surrounding tissue.

DETAILED DESCRIPTION OF THE PREFERRED EMBODIMENTS

Figure 1A:
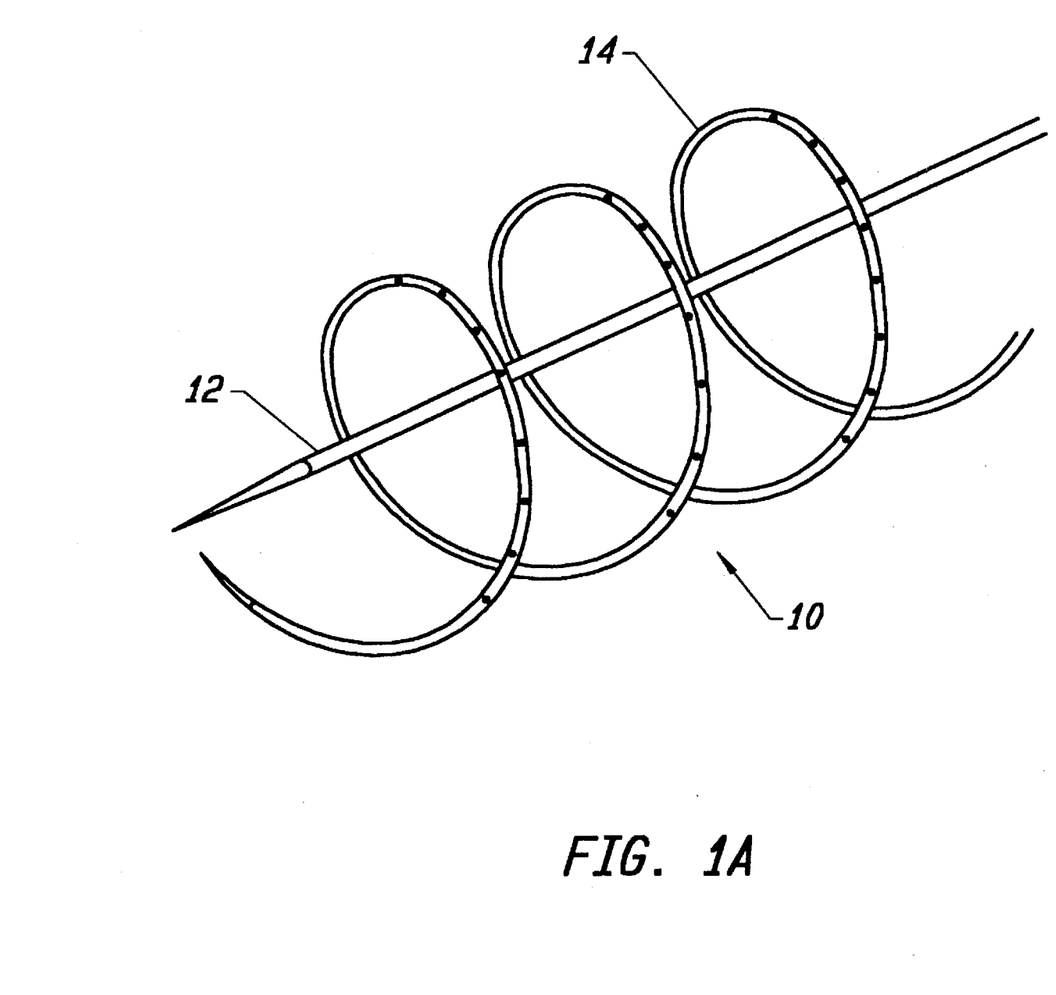
FIG. 1(a) is a perspective view of the RF treatment apparatus of the invention with the indifferent and active electrodes.
Figure 1B:
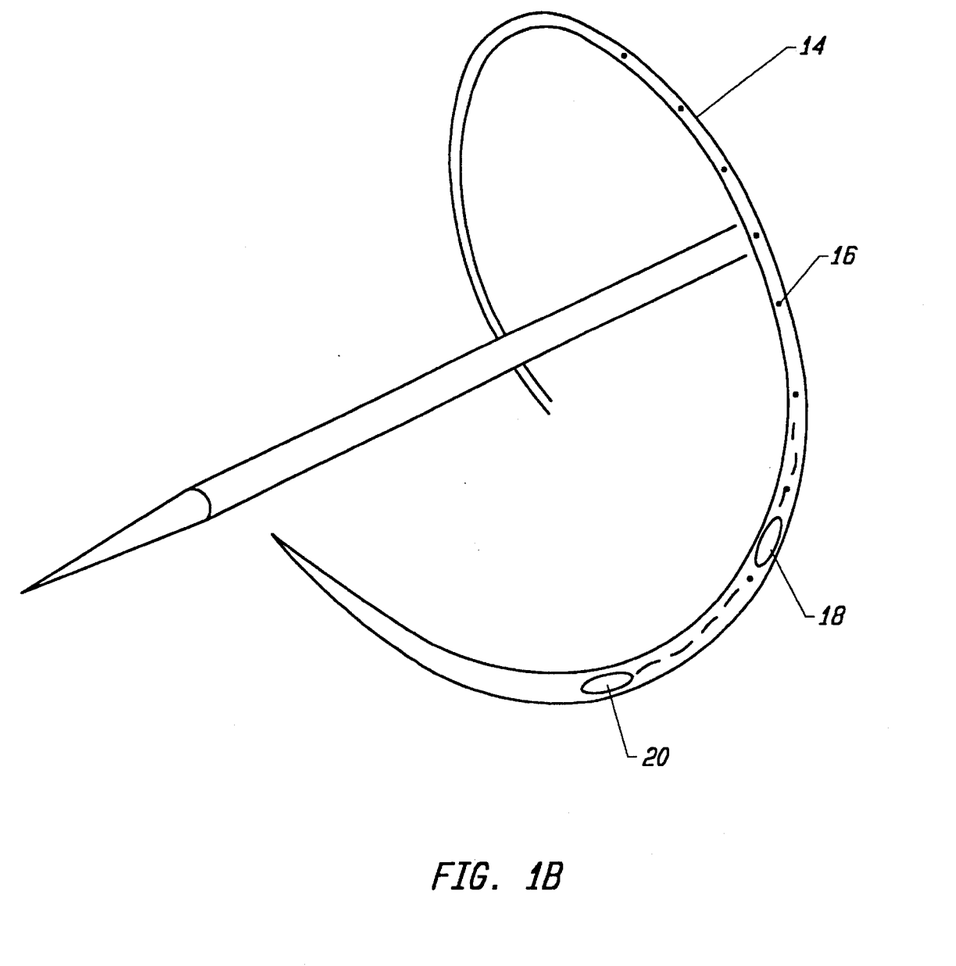
FIG. 1(b) is a perspective view of the conductive surface of the indifferent electrode according to the invention.
Figure 1C:
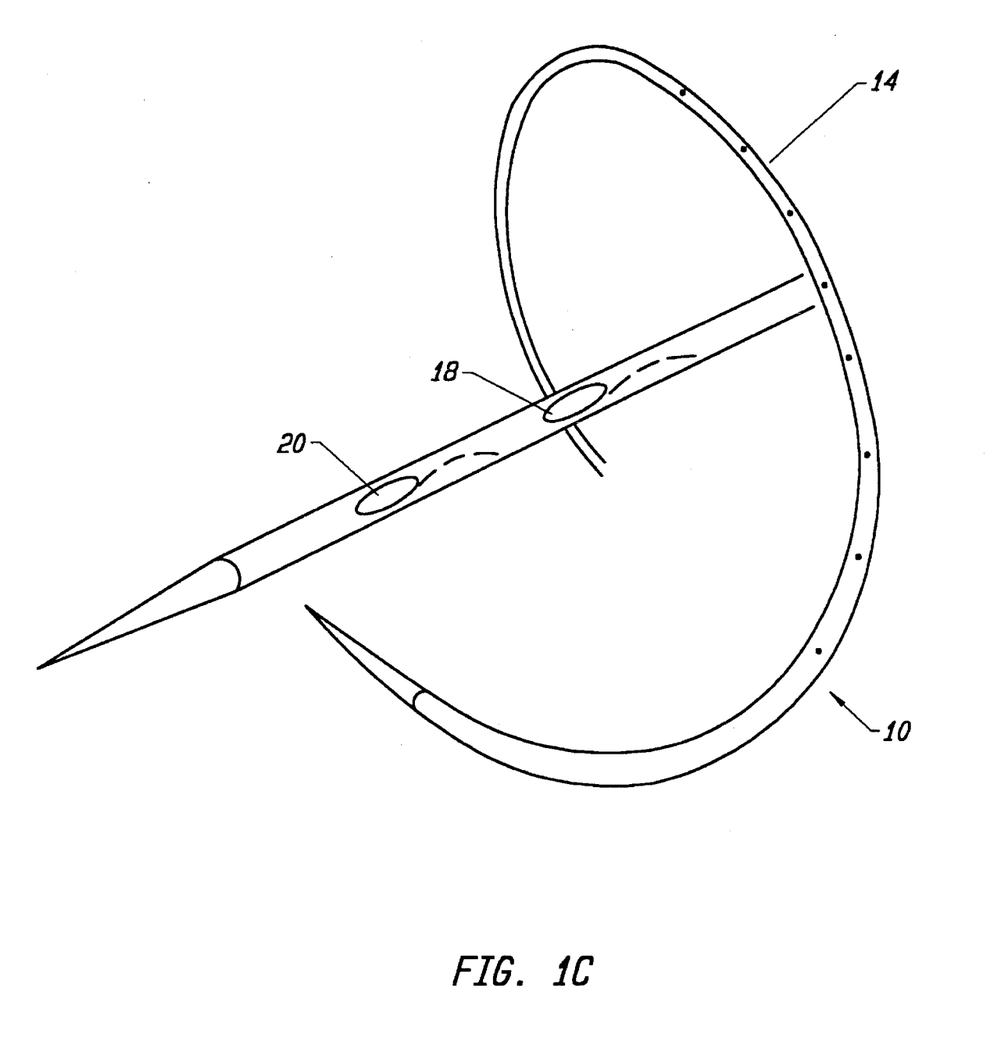
FIG. 1(c) is a perspective view of the conductive surface of the active electrode according to the invention.

Referring to FIGS. 1(a), 1(b) and 1(c), a multi-modality RF treatment apparatus 10, used for the treatment of a tumor or other selected tissue mass, includes an active electrode 12 and an indifferent electrode 14 as illustrated. Indifferent electrode 14 is shown in a deployed position and is in a generally coiled expanded geometry. It can form a helix. Active electrode 12 is adapted to be inserted into the interior of a tumor while indifferent electrode 14 is introduced, preferably through an introducing catheter, to an area adjacent to the tumor. It is then advanced, and as it exits from the introducing catheter, its distal end becomes deployed and expanded. Indifferent electrode 14 begins to wind itself around the outside surface of the tumor in a contacting relationship. The amount of indifferent electrode 14 that surrounds the tumor can vary. It can wind around only a portion of the tumor, all of it, it can cover substantially the entire exterior surface of the tumor, or only a small portion of it.

Indifferent electrode 14 has four or less coils in the deployed state. Preferably, it has three or less.

Active electrode 12 and indifferent electrode 14 are coupled to an RF power source, not shown in these Figures. RF treatment apparatus 10 can be monopolar or bipolar. Active electrode 12 delivers a controllable and variable amount of RF energy that is used to ablate the tumor. Indifferent electrode 14 can be used as a hyperthermia apparatus to deliver thermal energy inward towards the interior of the tumor and, additionally, in an outward direction, away from the tumor. This delivery of thermal energy serves to kill feeders from the tumor that may extend into tissue surrounding the tumor. Indifferent electrode 14 can also be a microwave antenna, coupled to a microwave source, to deliver thermal energy to the site following ablation of the tumor.

There are certain applications in which the two electrodes can switch functions, and electrode 12 becomes the indifferent electrode, and electrode 14 becomes the active electrode.

Indifferent electrode 14 is preferably hollow and includes a plurality of fluid distribution ports 16 from which a chemotherapeutic agent or electrolytic solution can be delivered to the tumor and surrounding tissue. Indifferent electrode 14 can be flat, round, cylindrical or of different geometric configurations. Active electrode 12 can be of any one of a number of different geometric configurations, but it is preferably cylindrical with a tapered distal end that provides for easy introduction into the tumor. Active electrode 12 can also be hollow and include one or more fluid distribution ports for introducing a variety of solutions, including but not limited to a chemotherapeutic agent or electrolytic solution.

One or more transponders or transducers 18 can be included on the exterior surfaces of electrodes 12 and 14 and coupled to an ultrasound source. Suitable transducers are well known to those skilled in the art. A transponder is a crystal that emits only, and sends a sonically visible signal to another crystal (transducer). Because of its simple function it can be relatively small. A transducer is a crystal that emits and reads the reflected signal that is bounced back to the crystal through a water medium.

Each transducer 18 can include a piezoelectric crystal mounted on a backing material. An ultrasound lens, fabricated an electrically insulating material, is mounted between the piezoelectric crystal and tissue. The piezoelectric crystal is connected by electrical leads to the ultrasound power source. Transducers 18 can be in the form of an imaging probe such as Model 21362, manufactured and sold by Hewlett Packard Company.

Additionally, one or more thermal sensors 20 can be included on the exterior surfaces of electrodes 12 and 14. Again, temperature sensors 20 are well known to those skilled in the art. Suitable temperature sensors include but are not limited to thermocouples, thermistors, IR fibers, and the like. Thermocouples and other type sensors may not be suitable for use in a microwave field. Fiber optic sensors can be used with microwave.

Figures 2, 3:
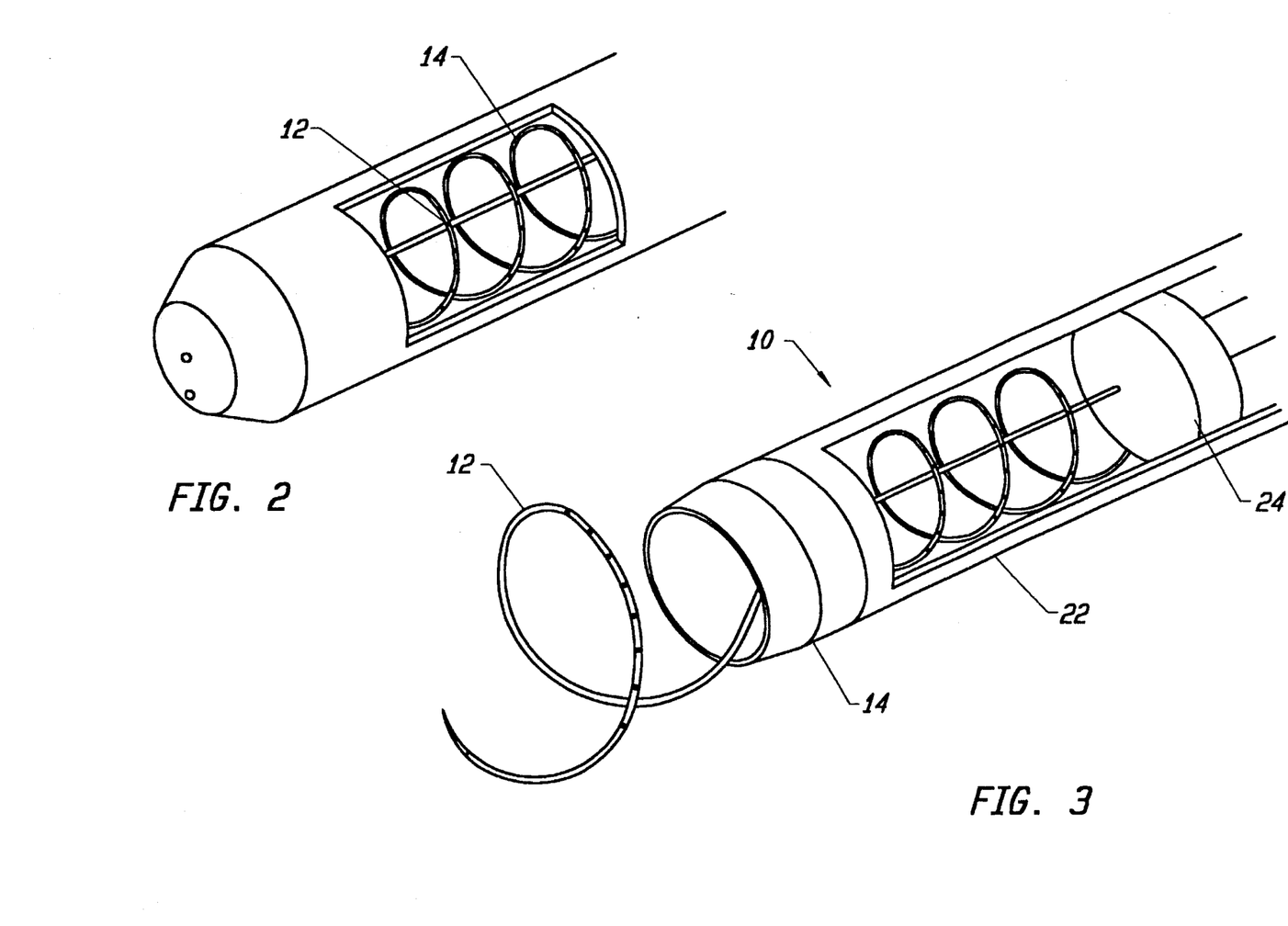
FIG. 2 is a cross-sectional view of the RF treatment apparatus of the invention with the indifferent electrode and active electrodes positioned in an introducing catheter. The indifferent electrode is in a non-deployed position.
FIG. 3 is a cross-sectional view of the RF treatment apparatus of the invention with the active electrode forming a helical structure when deployed out of the distal end of an introducing catheter. The inactive electrode is formed on the distal end of the introducing catheter.

In FIG. 2, indifferent electrode 14 is shown in a non-deployed state and is of a sufficiently small enough size to be positioned in a standard introducing or delivering catheter. A suitable introducing catheter is shown in FIG. 2. Its dimensions can vary depending on if the procedure is performed (i) percutaneously (1 to about 3.5 mm), or (ii) laprascopically (5 to 100 mm, preferably 8 mm).

In FIG. 3 indifferent electrode 14 is formed at the sharpened beveled end of introducing catheter 22. In this embodiment, indifferent electrode 14 can be a platinum band and the like. Active electrode 12 is the coiled electrode and is shown as being advanced out of introducing catheter 22 by the use of a cam member 24 which provides a pushing force against electrode 12. Cam 24 can also be used to retract and pull both of the electrodes out of, and unwind from, the tumor. As cam member 24 is retracted, it pulls electrodes 12 and 14 away from the tumor. In this manner, cam member 24 retracts either electrode 12 or 14 away from its helical deployed position and into a non-deployed, compacted position as the electrode enters introducing catheter 22.

Figures 4A, 4B:
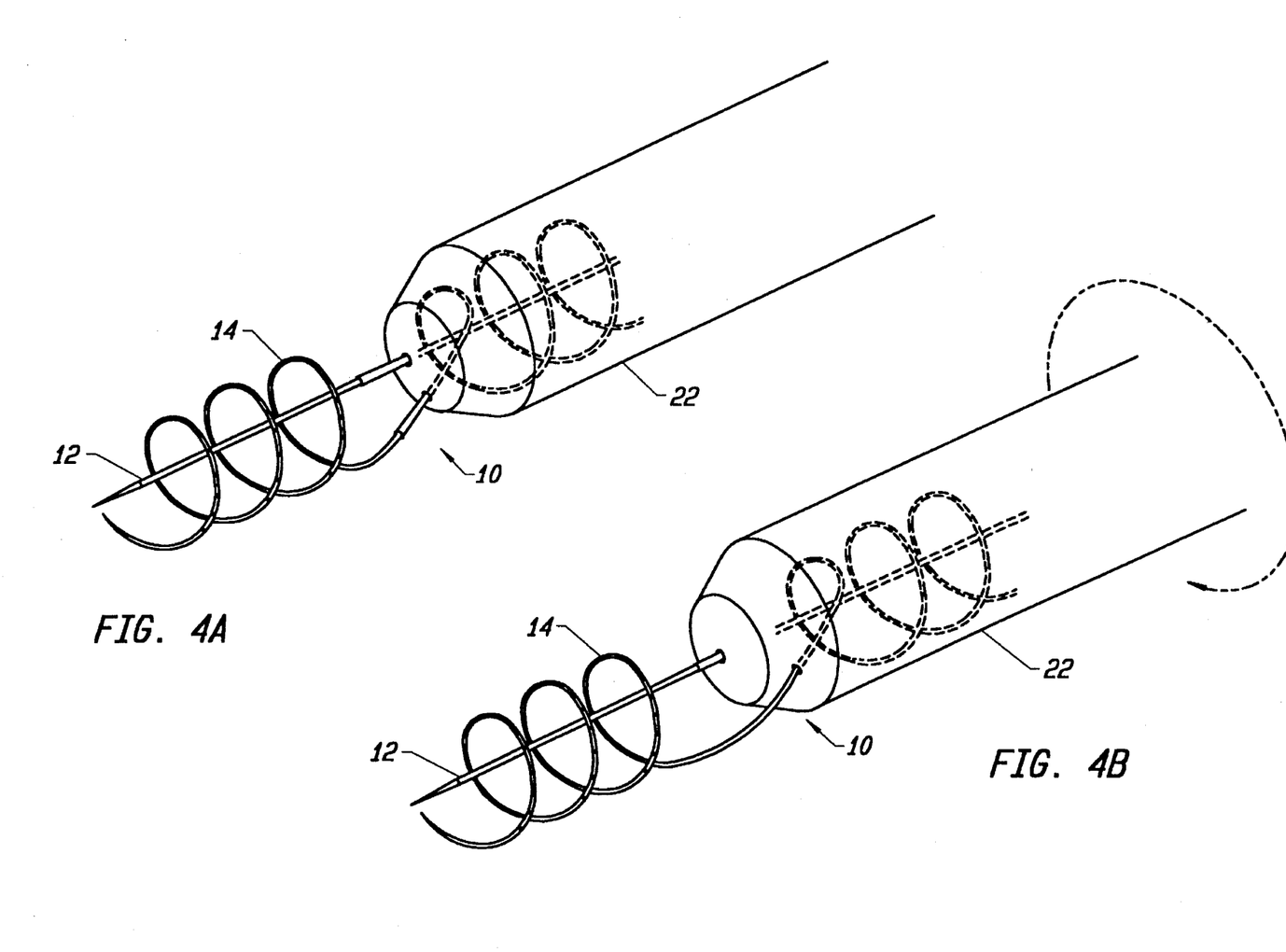
FIG. 4(a) is a perspective view of the RF treatment apparatus of the invention with the indifferent coiled electrode in a deployed state extending out of the distal end of the introducing catheter. In this deployed state, the indifferent electrode has two or three coils which surround the tumor.
FIG. 4(b) is a perspective view of the RF treatment apparatus of the invention. The indifferent electrode is deployed from a side of the introducing catheter.

In FIG. 4(*a*) indifferent electrode 14 is in a deployed state and extends out of the distal end of introducing catheter 22. Indifferent electrode 14 has only three coils in this Figure. As shown in FIG. 4(*b*), indifferent electrode 14 is deployed from a side of introducing catheter 22. As catheter 22 is turned, electrode 14 begins to unwind. The more catheter 22 is rotated, the more coils are formed and advanced from catheter 22. Additionally, a cam member 24 can be used to help advance both electrodes 12 and 14 out of catheter 22. Again, it will be appreciated that the coiled electrode can be either the active or indifferent electrode.

Indifferent electrode 14 can be made of a memory metal, such as a nickel titanium memory metal available from Raychem Corporation, Menlo Park, Calif. A resistive heating element can be positioned in an interior lumen of electrode 14. Resistive heating element can be made of a suitable metal that transfers heat to electrode 14, causing it to become coiled when the temperature of electrode 14 reaches a level that the memory metal is caused to deflect, as is well known in the art. Not all of electrode 14 need be made of the memory metal. Only that portion which coils around the tumor needs to become shaped. With the use of a memory metal, electrode 14 can be self-deployed as it is advanced out of delivery catheter 22 at either elevated or lower temperatures.

Electrodes 12 and 14 can be formed of a variety of materials. The electrodes can be made of bio-comparable materials including various metals such as copper, and as previously mentioned, memory metals. Additionally, electrode 14 can become coiled with the application of a first current and uncoiled when a second current is applied.

Figure 5:
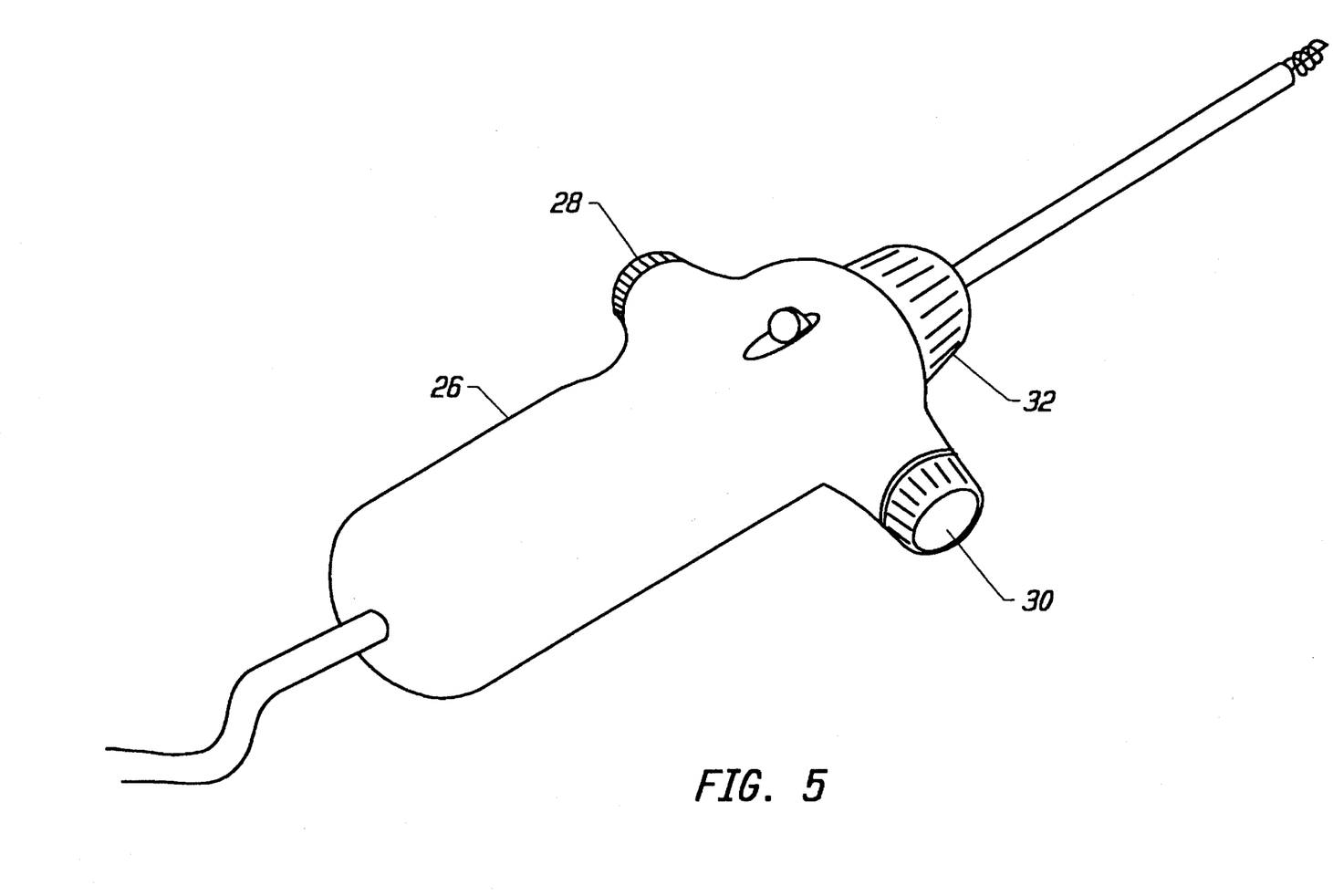
FIG. 5 is a perspective view of the RF treatment apparatus of the invention including a handpiece.

With reference now to FIG. 5, RF treatment apparatus 10 is shown and includes a handle 26 with actuators 28, 30 and 32 for a variety of different functions. For example, actuator 28 can advance or retract cam member 24 through introducing catheter 22. Actuator 30 can serve as a control for the introduction of fluids, such as a chemotherapeutic agent, to indifferent electrode 14. Additionally, actuator 32 may be used to switch indifferent electrode 14 from an RF electrode coupled to an RF energy source, to a microwave antenna coupled to a microwave source, and then back to an RF electrode.

Figure 6:
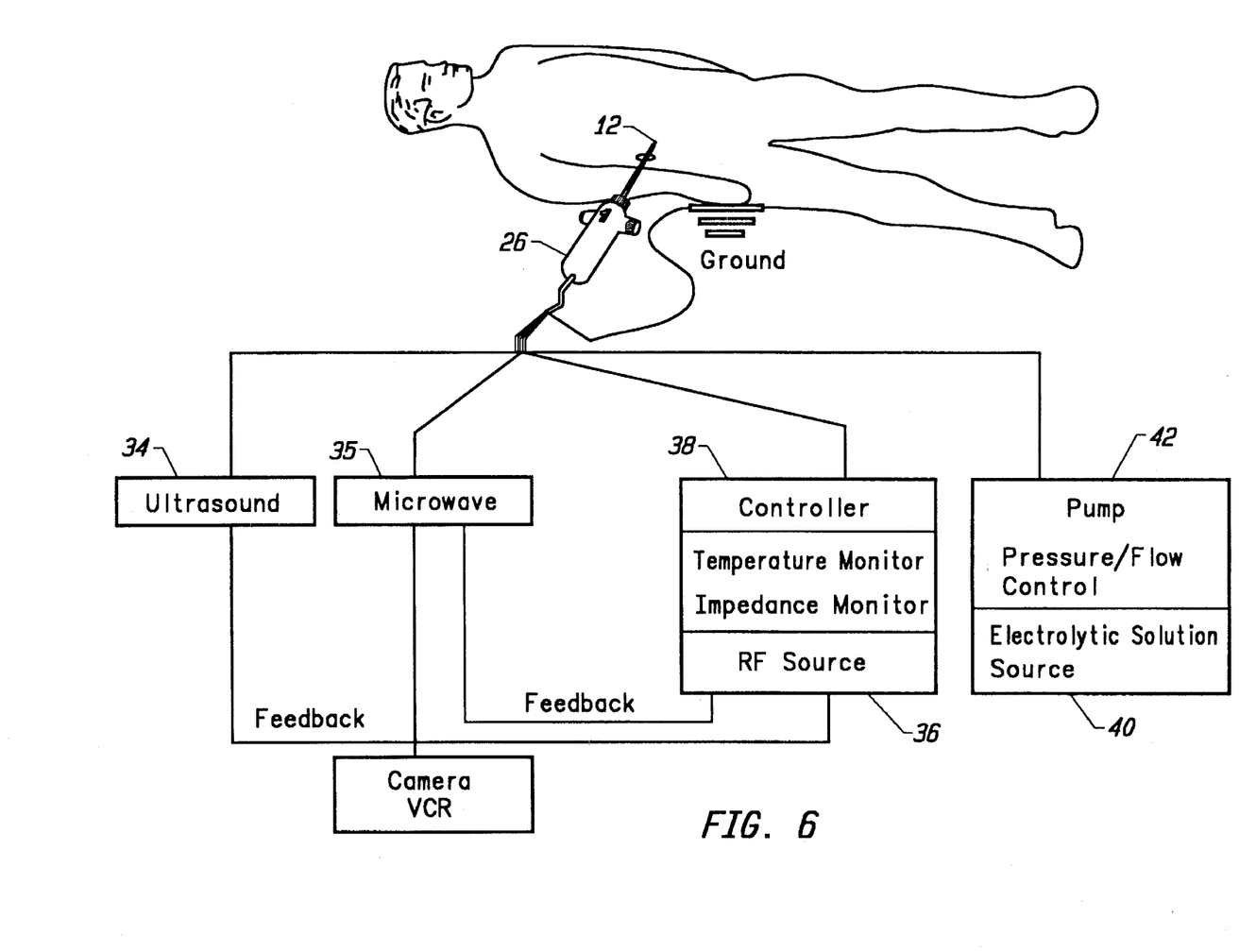
FIG. 6 is block diagram of the RF treatment apparatus of the invention including ultrasound, microwave, RF and chemotherapeutic sources, and a controller.

A schematic diagram of RF treatment apparatus 10 is shown in FIG. 6. Associated with treatment apparatus 10 is an ultrasound source 34 coupled to transducers 18, a microwave source 35, an optional optical system which can include a camera, VCR, viewing and illumination fibers and optics, and RF source 36 that can include a controller 38, a chemotherapeutic solution source 40 with associated pump, pressure/flow controls 42.

RF treatment apparatus provides multi-modality treatment for tumors and other selected tissue masses. Active electrode 12 provides RF ablation energy to the tumor. Indifferent electrode 14 is then switched from the function of being an RF indifferent electrode and becomes a microwave antenna coupled to microwave energy source 35. A suitable microwave energy source is well known to those skilled in the art. Electrode 14, now as a microwave antenna, provides a source of hyperthermia to the tumor as well as to tissue surrounding the exterior of the tumor site. Either or both electrodes 12 and/or 14 introduce a chemotherapeutic agent to the tissue site. Chemotherapy can begin before ablation, after ablation but before hyperthermia, or after hyperthermia. The various modalities can be repeated any number of times.

Figure 7:
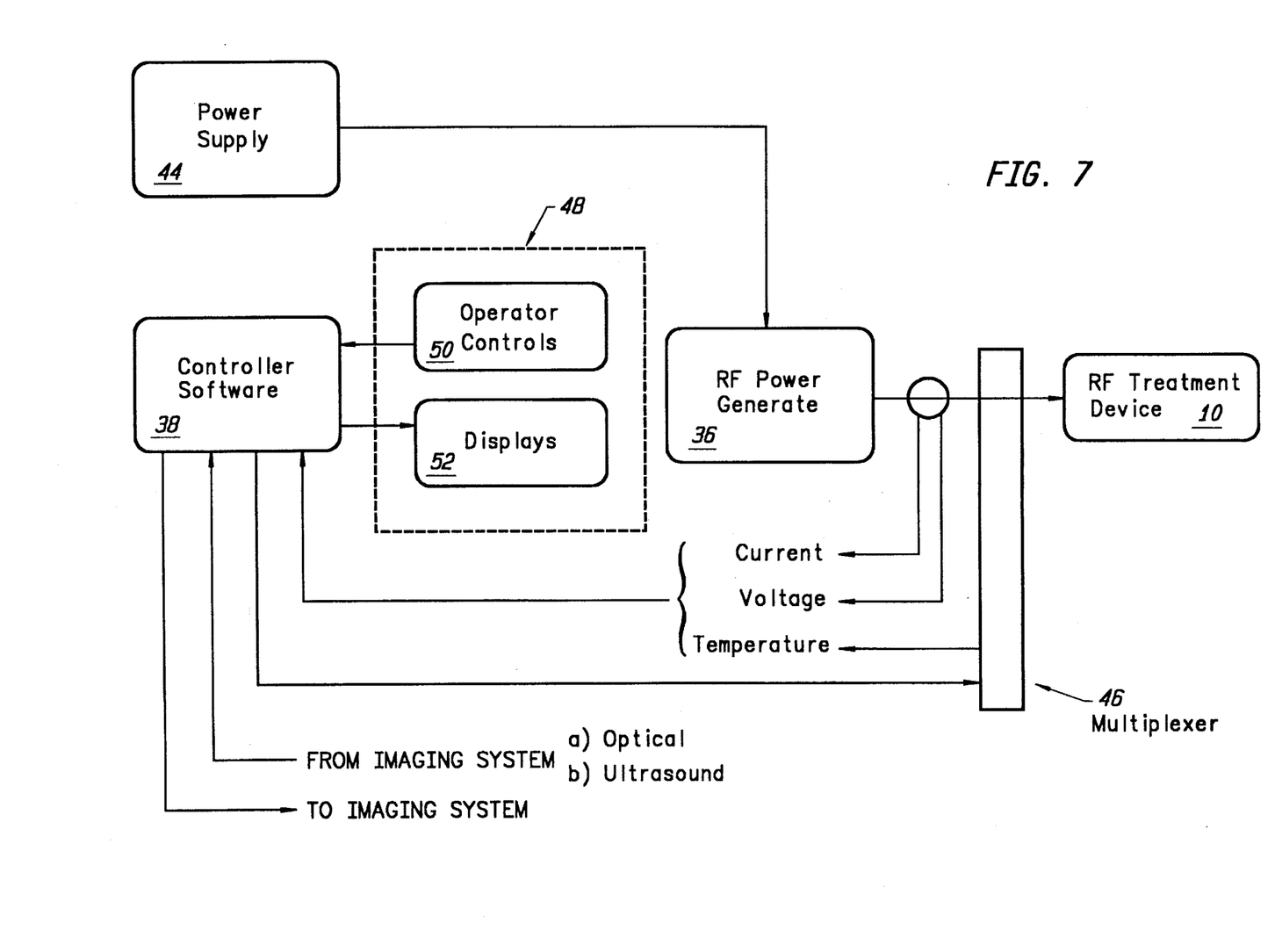
FIG. 7 is a block diagram of the RF treatment apparatus of the invention with a controller and multiplexer.

Referring now to FIG. 7, a power supply 44 delivers energy to RF power generator (source) 36 and then to RF treatment apparatus 10. Power supply 44 can also deliver energy to microwave source 35. A multiplexer 46 measures current, voltage and temperature (at the numerous temperature sensors). Multiplexer 46 is driven by controller 38, which can be a digital or analog controller, or a computer with software. When controller 38 is a computer it can include a CPU coupled through a system bus. On this system can be a keyboard, a disk drive, or other non-volatile memory systems, a display and other peripherals, as known in the art. Also coupled to the bus are a program memory and a data memory.

An operator interface 48 includes operator controls 50 and a display 52. Controller 38 is coupled to imaging systems, including transducers 18, temperature sensors 20, and viewing optics and optical fibers if included.

Current and voltage are used to calculate impedance. Diagnostics are done either optically or through ultrasound. Diagnostics can be performed both before and after treatment.

Temperature sensors 20 and sensors contained within RF source 36 measure voltage and current that is delivered. The output of these sensors is used by controller 38 to control the delivery of RF and microwave power. Controller 38 can also control temperature and power. The amount of RF and microwave energy delivered controls the amount of power. A profile of power delivered can be incorporated in controller 38, as well as a pre-set amount of energy to be delivered can also be profiled.

Feedback can be the measurement of impedance and/or temperature and occurs either at controller 38 or at RF source 36 if it incorporates a controller. For impedance measurement, this can be achieved by supplying a small amount of non-therapeutic RF energy. Voltage and current are then measured to confirm electrical contact.

Circuitry, software and feedback to controller 38 result in process control and are used to change, (i) power, including RF, microwave, ultrasound and the like, (ii) the duty cycle (on-off and wattage), (iii) mono-polar or bi-polar energy delivery, (iv) chemotherapeutic agent delivery, flow rate and pressure and (v) determine what ablation is completed through time, temperature and/or impedance. These process variables can be controlled and varied based on temperature monitored at multiple sites, and impedance to current flow that is monitored, indicating changes in current carrying capability of the tissue during the ablative process.

Figure 8:
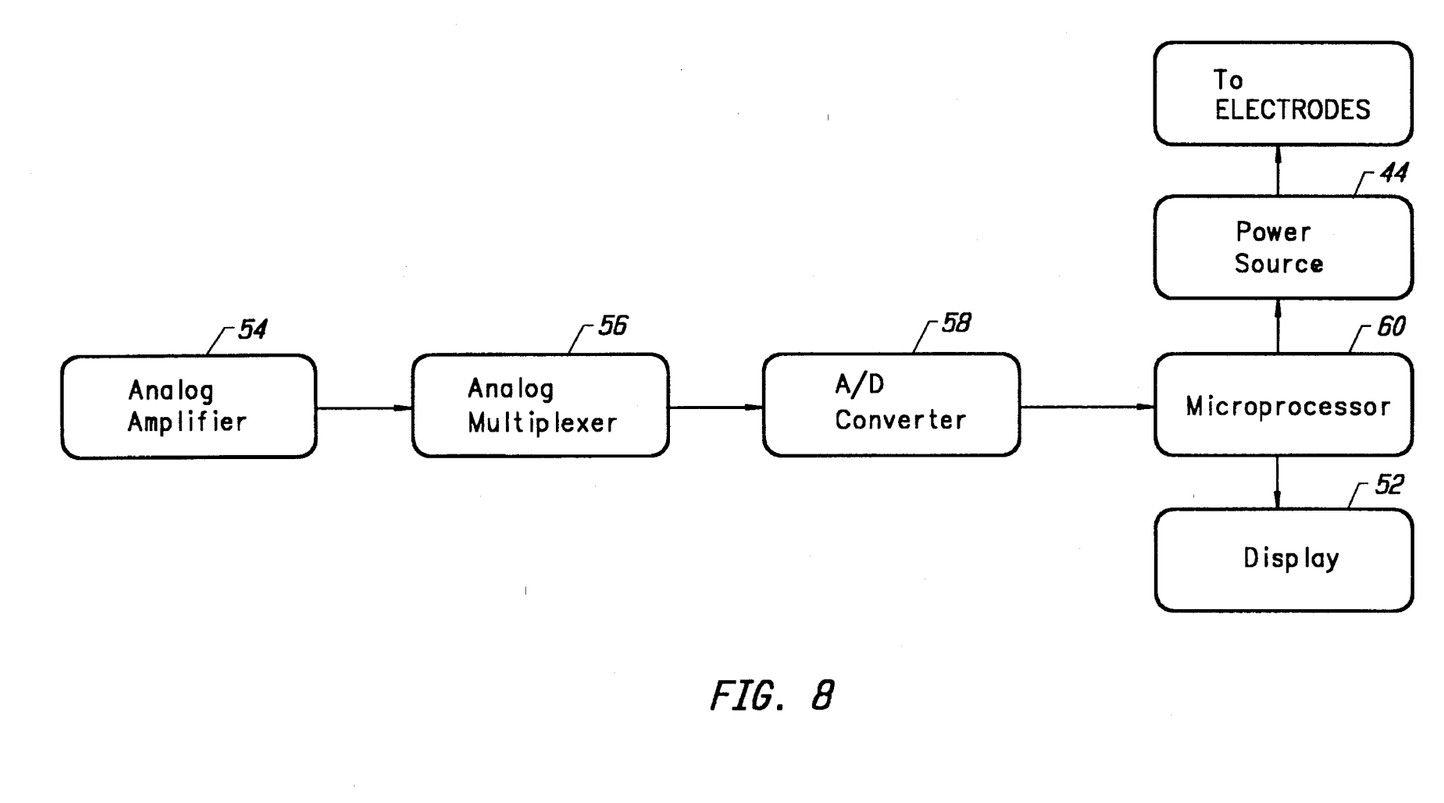
FIG. 8 is a block diagram of one embodiment of a system for processing outputs from temperature sensors and ultrasound transducers.

A block diagram of one embodiment of suitable processing circuitry is shown in FIG. 8. Temperature sensors 20 and transducers 18 are connected to the input of an analog amplifier 54. Temperature sensors 20 can be thermistors which have a resistance that varies with temperature. Analog amplifier 54 can be a conventional differential amplifier circuit for use with thermistors and transducers. The output of analog amplifier is sequentially connected by an analog multiplexer 56 to the input of an analog to digital converter 58. The output of amplifier 54 is a voltage which represents the respective sensed temperatures. The digitized amplifier output voltages are supplied by analog-to-digital converter 58 to a microprocessor 60 can be a type 68000. However, it will be understood that any suitable microprocessor or general purpose digital or analog computer can be used to calculate impedance or temperature.

Microprocessor 60 sequentially receives and stores digital representations of impedance and temperature. Each digital value received by microprocessor 60 corresponds to different temperatures and impedances.

Calculated temperature and impedance values can be indicated on display 52. Alternatively, or in addition to the numerical indication of temperature or impedance, calculated impedance and temperature values can be compared by microprocessor 60 with temperature and impedance limits. When the values exceed predetermined temperature or impedance values, a warning can be given on display 52, and additionally, the delivery of RF energy is then reduced, modified, or interrupted. A control signal from microprocessor 60 can reduce the power level supplied by RF source 36.

Thus, controller 38 receives and stores the digital values which represent temperatures and impedances sensed. Calculated surface temperatures and impedances can be forwarded by controller 38 to display 52. If desired, the calculated surface temperature of tissue is compared with a temperature limit, and a warning signal can be sent to the display. Similarly, a control signal can be sent to RF power source 36 when temperature or impedance values exceed a predetermined level.

The foregoing description of preferred embodiments of the present invention has been provided for the purposes of illustration and description. It is not intended to be exhaustive or to limit the invention to the precise forms disclosed. Obviously, many modification and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. An RF treatment apparatus for treatment of a tumor, comprising:
    an RF indifferent electrode having a compacted, non-deployed state, and an expanded deployed state, the RF indifferent electrode forming a helical structure with one or more coils in the deployed state that surround an exterior of the tumor, the indifferent electrode becoming a microwave antenna when coupled to a microwave source;

an RF active electrode, wherein the RF active electrode is introduced at least partially into the tumor and the RF indifferent electrode is introduced in a surrounding relationship to the tumor prior to supplying RF energy to the electrodes;

a deployment apparatus for deploying the RF indifferent electrode from the non-deployed state to the expanded deployed state;

a switching device coupled to the RF indifferent electrode that permits the RF indifferent electrode to deliver microwave or RF energy;

an RF energy source coupled to the indifferent and active electrodes; and a microwave energy source coupled to the indifferent electrode.

2. The RF treatment apparatus of claim 1, wherein the indifferent electrode has three or less coils in the deployed state.

3. The RF treatment apparatus of claim 1, wherein the indifferent electrode is hollow and includes a plurality of fluid distribution ports.

4. The RF treatment apparatus of claim 3, wherein the indifferent electrode is coupled to a chemotherapeutic agent source.

5. The RF treatment apparatus of claim 1, wherein the active electrode is hollow and includes a plurality of fluid distribution ports.

6. The RF treatment apparatus of claim 5, wherein the active electrode is coupled to a chemotherapeutic agent source.

7. The RF treatment apparatus of claim 1, wherein the active electrode has a sharpened distal end.

8. The RF treatment apparatus of claim 1, Wherein the indifferent electrode has a sharpened distal end.

9. The RF treatment apparatus of claim 1, further comprising:

at least one thermal sensor positioned on a surface of the indifferent electrode.

10. The RF treatment apparatus of claim 1, further comprising:

at least one thermal sensor positioned on a surface of the active electrode.

11. The RF treatment apparatus of claim 1, wherein the indifferent electrode is made of a memory metal.

12. The RF treatment apparatus of claim 1, wherein the indifferent electrode is made of nitinol.

13. An RF treatment apparatus for treatment of a tumor, comprising:

an introducing catheter with a catheter distal end and a catheter proximal end;

An RF indifferent electrode positioned at least partially in the introducing catheter in a compacted, non-deployed state, and advanced from the introducing catheter in an expanded deployed state, the RF indifferent electrode forming a helical structure with one or more coils in the deployed state that surround an exterior of the tumor, the indifferent electrode becoming a microwave antenna when coupled to a microwave source;

an active electrode positioned at least partially in the introducing catheter and advanced from the catheter distal end and introduced, wherein the RF active electrode is introduced at least partially into the tumor and the RF indifferent electrode is introduced in a surrounding relationship to the tumor prior to supplying RF energy to the electrodes;

a deployment apparatus for deploying the RF indifferent electrode from the nondeployed state to the expanded state; a switching device associated with the RF indifferent electrode that permits the RF indifferent electrode to deliver microwave or RF energy;

an RF energy source coupled to the indifferent and active electrodes; and a microwave energy source coupled to the indifferent electrode.

14. The RF treatment apparatus of claim 13, further comprising:

a handle attached to the proximal end of the introducing catheter.

15. The RF treatment apparatus of claim 14, wherein the deployment apparatus is an advancing cam positioned at least partially in the introducing catheter, the advancing cam attaching to a proximal end of the indifferent and active electrodes for advancing and retracting the indifferent and active electrodes in and out of the introducing catheter.

16. The RF treatment apparatus of claim 13, wherein the indifferent electrode has three or less coils in the deployed state.

17. The RF treatment apparatus of claim 13, wherein the indifferent electrode is hollow and includes a plurality of fluid distribution ports.

18. The RF treatment apparatus of claim 17, wherein the indifferent electrode is coupled to a chemotherapeutic agent source.

19. The RF treatment apparatus of claim 13, wherein the active electrode is hollow and includes a plurality of fluid distribution ports.

20. The RF treatment apparatus of claim 19, wherein the active electrode is coupled to a chemotherapeutic agent source.

21. The RF treatment apparatus of claim 13, wherein the active electrode has a sharpened distal end.

22. The RF treatment apparatus of claim 13, wherein the indifferent electrode has a sharpened distal end.

23. The RF treatment apparatus of claim 13, further comprising:

at least one thermal sensor positioned on a surface of the indifferent electrode.

24. The RF treatment apparatus of claim 13, further comprising:

at least one thermal sensor positioned on a surface of the active electrode.

25. The RF treatment apparatus of claim 13, wherein the indifferent electrode is made of a memory metal.

26. An RF treatment apparatus for treatment of a tumor, comprising:

an RF indifferent electrode having a compacted, non-deployed state, and an expanded deployed state, the RF indifferent electrode forming a helical structure with one or more coils in the deployed state that surround an exterior of the tumor;

an RF active electrode that is introduced into the tumor to provide RF ablation of the tumor, wherein the RF active electrode is introduced at least partially into the tumor and the RF indifferent electrode is introduced in a surrounding relationship to the tumor;

a deployment apparatus for deploying the RF indifferent electrode from the non-deployed state to the expanded deployed state; and an RF energy source coupled to the indifferent and active electrodes.

27. The RF treatment apparatus of claim 26, wherein the indifferent electrode has three or less coils in the deployed state.

28. The RF treatment apparatus of claim 26, wherein the indifferent electrode is hollow and includes a plurality of fluid distribution ports.

29. The RF treatment apparatus of claim 28, wherein the indifferent electrode is coupled to a chemotherapeutic agent source.

30. The RF treatment apparatus of claim 26, wherein the active electrode is hollow and includes a plurality of fluid distribution ports.

31. The RF treatment apparatus of claim 30, wherein the active electrode is coupled to a chemotherapeutic agent source.

32. The RF treatment apparatus of claim 26, wherein the active electrode has a sharpened distal end.

33. The RF treatment apparatus of claim 26, wherein the indifferent electrode has a sharpened distal end.

34. An RF treatment apparatus for treatment of a tumor, comprising;

an RF active electrode having a compacted, non-deployed state, and an expanded deployed state, the RF active electrode forming a helical structure with one or more coils in the deployed state that surround an exterior of the tumor;

an RF indifferent electrode that is introduced into the tumor to provide RF ablation of the tumor, wherein the RF indifferent electrode is introduced at least partially into the tumor and the RF active electrode is introduced in a surrounding relationship to the tumor;

a deployment apparatus for deploying the RF active electrode from the non-deployed state to the expanded deployed state; and an RF energy source coupled to the indifferent and active electrodes.

35. The RF treatment apparatus of claim 34, wherein the active electrode has three or less coils in the deployed state.

36. The RF treatment apparatus of claim 34, wherein the active electrode is hollow and includes a plurality of fluid distribution ports.

37. The RF treatment apparatus of claim 36, wherein the active electrode is coupled to a chemotherapeutic agent source.

38. The RF treatment apparatus of claim 34, wherein the indifferent electrode is hollow and includes a plurality of fluid distribution ports.

39. The RF treatment apparatus of claim 38, wherein the indifferent electrode is coupled to a chemotherapeutic agent source.

40. The RF treatment apparatus of claim 34, wherein the indifferent electrode has a sharpened distal end.

41. The RF treatment apparatus of claim 34, wherein the active electrode has a sharpened distal end.

* * * * *